United States Patent [19]

Buono et al.

[11] 4,135,945
[45] Jan. 23, 1979

[54] PIGMENT DISPERSIONS CONTAINING POLYOXYMETHYLENEOXAZOLIDINE BIOCIDES

[75] Inventors: Frederick J. Buono, Robbinsville; William B. Woods, Lebanon, both of N.J.

[73] Assignee: Tenneco Chemicals, Inc., Saddle Brook, N.J.

[21] Appl. No.: 826,590

[22] Filed: Aug. 22, 1977

[51] Int. Cl.$^2$ .............................................. C08L 79/04
[52] U.S. Cl. ........................... 106/308 N; 106/288 Q; 106/300; 106/288 B
[58] Field of Search ................ 106/308 N, 288 Q, 300

[56] References Cited

U.S. PATENT DOCUMENTS

| | | | |
|---|---|---|---|
| 2,893,886 | 7/1959 | Erskine et al. | 106/308 N |
| 3,890,264 | 6/1975 | Sidi et al. | 260/45.8 NZ |

Primary Examiner—Winston A. Douglas
Assistant Examiner—J. V. Howard
Attorney, Agent, or Firm—Evelyn Berlow

[57] ABSTRACT

Aqueous pigment dispersions that have improved resistance to microbial attack contain a biocidally-effective amount of a polyoxymethyleneoxazolidine selected from the group consisting of (a) compounds having the structural formula

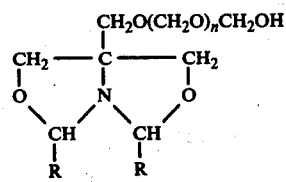

wherein each R represents hydrogen, alkyl of 1 to 6 carbon atoms, phenyl, halophenyl, or —(CH$_2$O)$_m$CH$_2$OH; m represents a number in the range of 0 to 2; and n represents a number in the range of 1 to 4;

(b) compounds having the structural formula

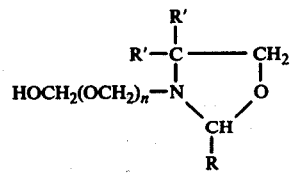

wherein each R' represents alkyl of 1 to 6 carbon atoms or —CH$_2$OH and R and n have the aforementioned significance; and (c) mixtures thereof.

6 Claims, No Drawings

PIGMENT DISPERSIONS CONTAINING POLYOXYMETHYLENEOXAZOLIDINE BIOCIDES

This invention relates to aqueous pigment dispersions having improved resistance to deterioration resulting from attack by bacteria, fungi, and other microorganisms. More particularly, it relates to aqueous pigment dispersions that contain a biocidally-effective amount of a polyoxymethyleneoxazolidine. It further relates to a method of preserving aqueous pigment dispersions.

Aqueous pigment dispersions, which are used in the manufacture of printing inks, paints, and the like, generally contain as dispersants and surfactants organic materials that render them susceptible to attack by bacteria, fungi, and other microorganisms. Microbiological deterioration of the pigment dispersions may be manifested as slime formation and/or as a change in the color, odor, and other properties of the dispersions.

To be useful as a preservative for aqueous pigment dispersions, a biocide should be effective against a wide variety of microorganisms at low concentrations for long periods of time; it should be effective over a wide range of pH values; it should be stable and soluble to some degree in water; it should not adversely affect the properties of the pigment dispersions or of compositions to which the dispersions are added; it should be non-toxic and non-irritating under the conditions of use; and it should provide protection from microbial degradation at a low cost.

A number of materials have been proposed as preservatives for aqueous pigment dispersions, but none has met all of the aforementioned requirements. Some do not provide the prolonged protection against attack by microorganisms, others adversely affect the properties of compositions to which the dispersions are added, and still others are hazardous to the health of those who come into contact with the dispersions or are relatively expensive as compared to the other components of the dispersions.

In accordance with this invention, it has been found that certain polyoxymethyleneoxazolidines meet all of the requirements that have been established for preservatives for aqueous pigment dispersions. These polyoxymethyleneoxazolidines provide aqueous pigment dispersions with excellent and prolonged resistance to deterioration resulting from attack by microorganisms at pH's ranging from about 7.5 through 12.0 without adversely affecting the properties of the dispersions or of compositions to which the dispersions are added at a relatively low cost and without appreciable hazard to those who handle the dispersions or compositions to which they have been added.

The polyoxymethyleneoxazolidines that can be used as preservatives for aqueous pigment dispersions include (a) compounds having the structural formula

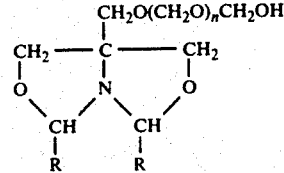

wherein each R represents hydrogen, alkyl of 1 to 6 carbon atoms, phenyl, halophenyl, or —$(CH_2O)_m$C-$H_2OH$; m represents a number in the range of 0 to 2; and n represents a number in the range of 1 to 4;

(b) compounds having the structural formula

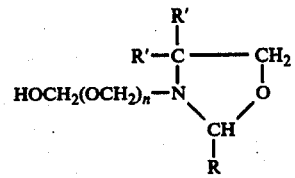

wherein each R' represents alkyl of 1 to 6 carbon atoms or —$CH_2OH$ and R and n have the aforementioned significance; and (c) mixtures of these compounds.

Illustrative of the bicyclic polyoxymethyleneoxazolidines that are effective as preservatives for aqueous pigment dispersions are 5-[hydroxymethyl-di(oxymethylene)]-1-aza-3,7-dioxabicyclo(3,3,0)octane, 5-[hydroxymethyl-tri(oxymethylene)]-1-aza-3,7-dioxabicyclo(3,3,0)octane, 2-phenyl-5-[hydroxymethyl-tetra(oxymethylene)]-1-aza-3,7-dioxabicyclo(3,3,0)octane, 2,8-bis(α-chloroethyl)-5-[hydroxymethyl-penta(oxymethylene)]-1-aza-3,7-dioxabicyclo(3,3,0)octane, 2,8-bis(p-chlorophenyl)-5-[hydroxymethyltri(oxymethylene)]-1-aza-3,7-dioxabicyclo(3,3,0)octane, 2-hydroxymethyl-5-[hydroxymethyl-tetra(oxymethylene)-1-aza-3,7-dioxabicyclo(3,3,0)octane, 2,8-bis(2-ethylbutyl)-5-[hydroxymethyltri(oxymethylene)]-1-aza-3,7-dioxabicyclo(3,3,0)octane, and 2,8-bis(hydroxymethyl)-5-[hydroxymethyl-di(oxymethylene)]-1-aza-3,7-dioxabicyclo(3,3,0)octane. Examples of the useful monocyclic polyoxymethyleneoxazolidines include 3-hydroxymethyloxymethylene-4,4-dimethyloxazolidine, 3-[hydroxymethyl-di(oxymethylene)]-4,4-diethyloxazolidine, 3-[hydroxymethyl-tri(oxymethylene)]-4,4-diethyloxazolidine, 3-[hydroxymethyl-tetra(oxymethylene)]-4-methyl-4-isopropyloxazolidine, 2-hexyl-3-[hydroxymethyltri(oxymethylene)]-4,4-di(hydroxymethyl)oxazolidine, 2-phenyl-3-[hydroxymethyl-di(oxymethylene)]-4-hexyl-4-hydroxymethyloxazolidine, 2-p-chlorophenyl-3-(hydroxymethyloxymethylene)-4,4-di(hydroxymethyl)oxazolidine, 2-hydroxymethyl-3-[hydroxymethyl-di(oxymethylene)]-4,4-dibutyloxazolidine, and 2,3-bis(hydroxymethyloxymethylene)-4,4-dimethyloxazolidine.

The preferred compounds for use as preservatives for aqueous pigment dispersions are those in which the total number of oxymethylene (—$CH_2O$—) units in one or more of the substituents on the oxazolidine rings is not greater than six. While compounds having more than six oxymethylene units in their ring substituents are very effective in controlling the growth of bacteria and fungi, they tend to be somewhat unstable in pigment dispersions and to impart to them the odor of formaldehyde. Examples of the preferred bicyclic compounds include polyoxymethyleneoxazolidines in which (i) the substituent in the 5-position is —$CH_2O$—(C-$H_2O)_{1-4}CH_2OH$ and the substituents in the 2- and 8-positions are hydrogen, alkyl, phenyl, or halophenyl;

(ii) the substituent in the 5-position is —$CH_2OCH_2OCH_2OH$, that in the 2-position is —$(CH_2O)_{0-2}$-$CH_2OH$, and that in the 8-position is hydrogen, alkyl, phenyl, or halophenyl;

(iii) the substituent in the 5-position is —(CH$_2$O(CH$_2$O)$_{1-2}$CH$_2$OH and the substituents in the 2- and 8-positions are —CH$_2$OH.

Examples of the preferred monocyclic compounds include polyoxymethyleneoxazolidines in which (i) the substituent in the 2-position is hydrogen, alkyl, phenyl, or halophenyl, that in the 3-position is —(CH$_2$O)$_{1-4}$CH$_2$OH, and those in the 4-position are alkyl;

(ii) the substituent in the 2-position is —(CH$_2$O)$_{0-3}$CH$_2$OH that in the 3-position is —CH$_2$OCH$_2$OH, and those in the 4-position are alkyl;

(iii) the substituent in the 2-position is —CH$_2$OH, that in the 3-position is —(CH$_2$O)$_{1-2}$CH$_2$OH, and one or both of those in the 4-position are —CH$_2$OH.

It is particularly preferred that the pigment dispersions contain a biocide that comprises one or more polyoxymethyleneoxazolidines having the structural formula

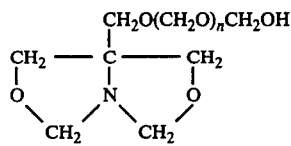

wherein n represents a number in the range of 1 to 4.

The preparation and properties of polyoxymethyleneoxazolidines were described in detail by Sidi and Johnson in U.S. Pat. No. 3,890,264, which is incorporated herein by reference.

Especially advantageous results have been obtained when aqueous solutions that contain 20% to 80% by weight and preferably 40% to 60% by weight of one or more of the aforementioned polyoxymethyleneoxazolidines are used to protect pigment dispersions from attack by microorganisms. In addition to costing less to produce than purified polyoxymethyleneoxazolidines and being easier to incorporate into dispersions, the aqueous solutions provide better biocidal activity for a given concentration of the compounds in the pigment dispersions.

The amount of the polyoxymethyleneoxazolidines used is that required to impart the desired level of protection from microbial attack to the pigment dispersions. As little as 0.02% by weight of the biocide will ordinarily bring about an appreciable improvement in the resistance of the dispersions to attack by microorganisms. Two percent of more of the biocidal component may be used when protection over an extended period of time is required. In most cases, 0.1% to 1% by weight of polyoxymethyleneoxazolidine is used to protect the aqueous pigment dispersions from attack by microorganisms.

The polyoxymethyleneoxazolidines can be used to impart microbial resistance to a wide variety of aqueous pigment dispersions that are normally susceptible to degradation resulting from attack by bacteria, fungi, and other microorganisms. These aqueous pigment dispersions generally contain about 20% to 75% by weight of a pigment component, 0.2% to 15% by weight of a surfactant component, and 20% to 75% by weight of water.

The pigment component of the dispersions may contain organic pigments, inorganic pigments, extender pigments, or mixtures thereof. Illustrative of the organic pigments that may be present are phthalocyanine pigments such as Phthalocyanine Blue and Phthalocyanine Green, quinacridone pigments such as Monastral Red Y and Quindo Magenta, vat pigments such as Carbazol Violet and Hydron Blue RG, and azo pigments such as the Lithol reds and BON reds. Examples of the useful inorganic pigments include titanium dioxide, zinc oxide, aluminum oxide, magnesium oxide, iron oxides, chromium oxides, zinc sulfides, cadmium sulfides, cadmium selenides, ultramarine blue, lead chromate, and carbon blacks. Examples of the extender pigments that may be present include clay, calcium carbonate, talc, bentonite, kaolin, mica, silica, asbestos, barium sulfate, and barium carbonate.

The surfactant component comprises one or more of the surfactants, dispersants, emulsifiers, wetting agents, protective colloids, and solvents that are conventionally used in the production of aqueous pigment dispersions. Illustrative of the useful dispersants, surfactants, emulsifiers, and wetting agents are the addition products of ethylene oxide or propylene oxide with a monohydric alcohol having 6 to 20 carbon atoms such as lauryl alcohol or ricinoleyl alcohol, with a polyhydric alcohol such as ethylene glycol, propylene glycol, glycerol, trimethylolpropane, pentaerythritol, or sorbitol, with a phenol such as p-nonylphenol or p-benzyl-o-phenylphenol; alkyl polyoxyalkylene ethanols, alkyl polyoxyalkylene propanols, and alkyl phenoxypolyoxyalkylene ethanols wherein the alkyl group is a C$_4$–C$_{10}$ carbon chain and the polyoxyalkylene groups number from 8 to 50 and are either ethylene oxide or propylene oxide adducts; alkali metal and ammonium salts of copolymers of maleic anhydride and diolefins, such as diisobutylene; alkyl and aralkyl ethers of alkylene glycols; alkyl aryl sulfonates; amine salts of alkylbenzene sulfonic acids; ethoxylated alkyl sulfonates; alkali metal and ammonium polyphosphates; alkylamines, alkanolamines; lignosulfonates; ammonium and alkali metal salts of fatty acids; and ammonium and alkali metal salts of alkylphosphates. Protective colloids that may be present include polyvinyl alcohol, sodium polyacrylate, sulfonated naphthalene derivatives, alginates, casein, methylcellulose, hydroxyethylcellulose, carboxymethylcellulose, gelatin, glue, and starch. The surfactant component may also contain a solvent that may be an alcohol such as methanol, ethanol, cyclohexanol, 3-methoxybutanol, ethylene glycol, hexylene glycol, or diacetone alcohol; a hydrocarbon such as benzene, toluene, xylene, mineral spirits, heptane, or naphtha; a ketone such as acetone, diacetone, methyl ethyl ketone, or methyl isobutyl ketone; or mixtures thereof. While a wide variety of compounds can be used in the surfactant component, the choice of compound or combination of compounds and the amount of each employed will depend upon such factors as the type of pigment in the dispersion, the amount of pigment present, and the conditions that will be encountered by the dispersion, and they are readily apparent to those having ordinary skill in this art.

The aqueous pigment dispersions of this invention may be produced by any suitable and convenient procedure. For example, the pigment component, surfactant component, and water may be mixed and ground together in a ball mill, pebble mill, dispersion mixer, colloid mill, or a high shear mixer. The biocidal component may be added before, during, or after the mixing step.

The invention is further illustrated by the following examples. In the examples, all parts are parts by weight and all percentages and percentages by weight.

EXAMPLE 1

A. A titanium dioxide slurry was prepared by mixing together the following materials:

|  | Parts |
|---|---|
| Titanium Dioxide | 62 |
| Octylphenoxypolyethoxyethanol | 1 |
| Water | 37 |

Small amounts of a biocidal component were added to portions of the slurry, and the resulting slurries were mixed thoroughly.

B. The biocide-containing titanium dioxide slurries were evaluated using the following procedures:

1. Broth cultures of *Pseudomonas aeruginosa, Aerobacter aerogenes, Bacillus subtilis, Bacillus megaterium,* and *Bacillus licheniformis* were prepared by incubation of inoculated Trypticase-soy broth (50 ml) contained in flasks.

After incubation for 18 to 24 hours at 35° C., an aliquot of the culture was removed from each flask and inoculated into 100 gram portions of the test material. The amount of inoculum added to the test material was such that the final level of bacteria was between $0.5 \times 10^6$ and $3 \times 10^6$ per gram of test material. After thorough mixing, the inoculated samples were incubated at 35° C. under 90 percent relative humidity. At intervals during the incubation, the samples were tested for the presence of viable bacteria. The viability test was carried out by adding an aliquot of the test material to Trypticase-soy broth, incubating for 48 hours at 35° C., and then streaking on a Trypticase-soy agar plate. After a 24 hour incubation period at 35° C., the plates were examined for growth along the streak. The results obtained are reported in Table I as + (growth present) or − (growth absent).

2. A mixed inoculum of three fungi isolated by standard microbiological techniques from contaminated titanium dioxide slurries was prepared by incubation of inoculated milk dilution bottles containing 50 ml. of solidified potato dextrose agar. After incubation at 28° C. for 24 hours, the cultures were removed from the agar surface, diluted with a phosphate buffer, and inoculated into 300 gram portions of the titanium dioxide slurry. After thorough mixing, the slurries were incubated at 28° C. under 90 percent relative humidity. At intervals during the incubation, the samples were tested for the presence of viable fungi. The viability test was carried out by adding an aliquot of the slurry to potato dextrose broth, incubating at 28° C. for 24 hours, streaking on potato dextrose agar, and after a 24 hour incubation period at 28° C., monitoring the plates for growth along the streak. The results are reported in Table II as + (growth present) or − (growth absent).

EXAMPLE 2

A titanium dioxide slurry was prepared by mixing together the following materials:

|  | Parts |
|---|---|
| Titanium Dioxide | 65 |
| Water | 34.4 |
| Octylphenoxypolyethoxyethanol | 0.3 |
| Potassium tributyl phosphate | 0.3 |

Small amounts of a biocidal component were added to portions of the slurry. The resulting slurries were mixed thoroughly and then evaluated by the procedures described in Example 1B. The results obtained are set forth in Tables I and II.

Table I

Activity of Biocides in Titanium Dioxide Slurries

| TiO₂ Slurry | Biocide* | Concentration of Biocide (%) | Bacterial Viability Incubation Period (Days) | | | | | | |
|---|---|---|---|---|---|---|---|---|---|
| | | | 1 | 2 | 3 | 5 | 7 | 14 | 21 |
| Product of Ex. 1 | None | — | + | + | + | + | + | + | + |
| | A | 0.25 | − | − | − | − | − | − | − |
| | | 0.10 | + | − | − | − | − | − | − |
| | | 0.05 | + | + | + | − | − | − | − |
| | B | 0.25 | − | − | − | − | − | − | − |
| | | 0.10 | − | − | − | − | − | − | − |
| | | 0.05 | + | + | − | − | − | − | − |
| Product of Ex. 2 | None | — | + | + | + | + | + | + | + |
| | A | 0.25 | − | − | − | − | − | − | − |
| | | 0.10 | − | − | − | − | − | − | − |
| | | 0.05 | + | − | − | − | − | − | − |
| | B | 0.25 | − | − | − | − | − | − | − |
| | | 0.10 | + | − | − | − | − | − | − |
| | | 0.05 | + | + | − | − | − | − | − |

*Biocide A = Aqueous solution containing 59.9% of solids shown by NMR analysis of the silyl ethers to be a mixture containing about 20% of 5-hydroxy-methyl-1-aza-3,7-dioxabicyclo(3,3,0)octane, 37% of5-hydroxymethoxymethyl-1-aza-3,7-dioxabicyclo-(3,3,0)octane, 14% of 5-[hydroxymethyl di(oxy-methylene)]-1-aza-3,7-dioxabicyclo(3,3,0)octane, 21% of 5-[hydroxymethyl tri(oxymethylene)]-1-aza-3,7-dioxabicyclo(3,3,0)octane, and 8% of 5-[hydroxymethyl tetra(oxymethylene)]-1-aza-3,7-dioxabicyclo(3,3,0)octane.
Biocide B = Comparative BiocideHexahydro-1,3,5-triethyl-s-triazine(Vancide TH)

Table II

Activity of Biocides in Titanium Dioxide Slurries

| TiO₂ Slurry | Biocide* | Concentration of Biocide (%) | Fungal Viability Incubation Period (Days) | | | | | | |
|---|---|---|---|---|---|---|---|---|---|
| | | | 1 | 2 | 3 | 5 | 7 | 14 | 21 |
| Product of Ex. 1 | None | — | + | + | + | + | + | + | + |
| | A | 0.25 | − | − | − | − | − | − | − |
| | | 0.10 | − | − | − | − | − | − | − |
| | | 0.05 | − | − | − | − | − | − | − |
| | B | 0.25 | − | − | − | − | − | − | − |
| | | 0.10 | − | − | − | − | − | − | − |
| | | 0.05 | − | − | − | − | − | − | − |
| Product of Ex. 2 | None | — | + | + | + | + | + | + | + |
| | A | 0.25 | − | − | − | − | − | − | − |
| | | 0.10 | + | − | − | − | − | − | − |
| | | 0.05 | + | + | + | − | − | − | − |
| | B | 0.25 | − | − | − | − | − | − | − |
| | | 0.10 | + | − | − | − | − | − | − |
| | | 0.05 | + | + | − | − | − | − | − |

*Biocide A = Aqueous solution containing 59.9% of solids shown by NMR analysis of the silyl ethers to be a mixture containing about 20% of 5-hydroxy-methyl-1-aza-3,7-dioxabicyclo(3,3,0)octane, 37% of 5-hydroxymethoxymethyl-1-aza-3,7-dioxabicyclo(3,3,0)octane, 14% of 5-[hydroxymethyl di(oxymethylene)]-1-aza-3,7-dioxabicyclo(3,3,0)octane, 21% of 5-[hydroxymethyl tri(oxymethylene)]-1-aza-3,7-dioxabicyclo(3,3,0)octane, and 8% of 5-[hydroxymethyl tetra(oxymethylene)]-1-aza-3,7-dioxabicyclo(3,3,0)octane.
Biociode B = Comparative Biocide Hexahydro-1,3,5-triethyl-s-triazine (Vancide TH)

From the data in Tables I and II, it will be seen that polyoxymethyleneoxazolidines are effective preservatives for aqueous titanium dioxide slurries that contain an organic surfactant component.

EXAMPLE 3

A. Aqueous pigment dispersions were prepared by mixing together the following materials:

|  | Parts |
|---|---|
| Organic pigment | 25 |
| Propylene glycol | 10 |
| Talc | 10 |
| Water | 53 |

-continued

| | Parts |
|---|---|
| Monobutyl ether of polyoxy-propylene-polyoxyethylene ethanol | 1 |
| Biocide | 0.2–1.0 |

The biocidal component that was incorporated into the pigment dispersions was a 50% aqueous solution of a mixture of polyoxymethyleneoxazolidines that contained about 10% of 5-hydroxymethyl-1-aza-3,7-dioxabicyclo(3,3,0)octane, 37% of 5-hydroxymethoxymethyl-1-aza-3,7-dioxabicyclo(3,3,0)octane, 24% of 5-[hydroxymethyl-di(oxymethylene)]-1-aza-3,7-dioxabicyclo(3,3,0)-octane, 21% of 5-[hydroxymethyl-tri(oxymethylene)]-1-aza-3,7-dioxabicyclo(3,3,0)octane, and 8% of 5-[hydroxymethyl-tetra(oxymethylene)]-1-aza-3,7-dioxabicyclo(3,3,0)octane.

B. The polyoxymethyleneoxazolidine-containing pigment dispersions were evaluated by the following procedure:

A bacterial inoculum consisting of equal parts of gram positive and gram negative bacteria that had been isolated from spoiled pigment dispersions was prepared by incubation of inoculated solidified Trypticase-soy agar (50 ml) contained in flasks. After incubation at 35° C. for 24 hours, the cultures were removed from the agar surface, diluted to an appropriate volume in phosphate buffer and inoculated into 300 gram portions of the pigment dispersions. The dispersions were challenged with a bacterial inoculum size sufficient to produce a concentration of $10^6$ bacterial cells per milliliter of pigment dispersion. After thorough mixing, the dispersions were incubated at 35° C. under 90 percent relative humidity. The dispersions were tested periodically for the presence of viable bacteria during the incubation period. After one and two weeks' incubation, the dispersions were challenged again with a bacterial inoculum. The results obtained in the viability tests are given in Table III.

From the data in Table III it will be seen that the polyoxymethyleneoxazolidines provided effective protection from microbial growth at concentrations between 0.2% and 1%.

Table III

Activity of Polyoxymethyleneoxazolidines as Biocides in Aqueous Pigment Dispersions

| Organic Pigment | Biocide Concentration % | Bacterial Viability | | | | | | | | | | | | | |
|---|---|---|---|---|---|---|---|---|---|---|---|---|---|---|---|
| | | 1st Challenge Viability (days) | | | | 2nd Challenge Viability (days) | | | | 3rd Challenge Viability (days) | | | | | |
| | | 1 | 2 | 3 | 5 | 7 | 1 | 2 | 3 | 5 | 7 | 1 | 2 | 3 | 5 | 7 |
| Blue | 0.2 | − | − | − | − | − | − | − | − | − | − | + | + | + | + | + |
| Yellow | 1.0 | − | − | − | − | − | − | − | − | − | − | + | − | − | − | − |
| | 0.5 | − | − | − | − | − | − | − | − | − | − | + | − | − | − | − |
| | 0.2 | − | − | − | − | − | − | − | − | − | − | + | − | − | − | − |
| | 0 | + | + | + | + | + | + | + | + | + | + | + | + | + | + | + |

EXAMPLE 4

A. A clay slurry was prepared by mixing together the following materials:

| | Parts |
|---|---|
| Clay (kaolin) | 68.0 |
| Water | 31.8 |
| Organic surfactant (polymeric alkyl phosphonate) | 0.2 |

The clay slurry was allowed to stand at 25° C. for one week during which time the population of those bacteria native to the clay system increased to approximately $10^6$/ml. After one week, small amounts of a biocidal component were added to portions of the slurry, and the resulting slurries were mixed thoroughly.

B. The biocide-containing clay slurries were evaluated using the following procedure:

At intervals during incubation at 35° C., the slurry samples were tested for the presence of viable bacteria. The viability test was carried out by adding an aliquot of the test material to Trypticase-soy broth, incubating for 48 hours at 35° C., and then streaking on a Trypticase-soy agar plate. After a 24 hour incubation period at 35° C., the plates were examined for growth along the streak. The results obtained are reported in Table V as + (growth present) or − (growth absent).

Table IV

Activity of Biocides in a Clay Slurry

| Clay Slurry | Biocide* | Concentration of Biocide (%) | Bacterial Viability Incubation Period (Days) | | | | | | |
|---|---|---|---|---|---|---|---|---|---|
| | | | 1 | 2 | 3 | 5 | 7 | 14 | 21 |
| Product of Ex. 4 | None | — | + | + | + | + | + | + | + |
| | A | 0.10 | + | − | − | − | − | − | − |
| | | 0.05 | + | + | − | − | − | − | − |
| | B | 0.10 | + | − | − | − | − | − | − |
| | | 0.05 | + | + | − | − | − | − | − |

*Biocide A = Aqueous solution containing 59.9% of solids shown by NMR analysis of the silyl ethers to be a mixture containing about 20% of 5-hydroxymethyl-1-aza-3,7-dioxabicyclo(3,3,0)octane, 37% of 5-hydroxymethoxymethyl-1-aza-3,7-dioxabicyclo-(3,3,0)octane, 14% of 5-[hydroxymethyl di(oxy-methylene)]-1-aza-3,7-dioxabicyclo(3,3,0)octane, 21% of 5-[hydroxymethyl tri (oxymethylene)]-1-aza-3,7-dioxabicyclo(3,3,0)octane, and 8% of 5-[hydroxymethyl tetra (oxymethylene)]-1-aza-3,7-dioxabicyclo(3,3,0)octane.16 Biocide B = Comparative BiocideHexahydro-1,3,5-triethyl-s-triazine(Vancide TH)

Each of the other polyoxymethyleneoxazolidines herein disclosed can be used in a similar way to protect aqueous pigment dispersions from microbial attack.

What is claimed is:

1. An aqueous pigment dispersion having improved resistance to attack by bacteria and fungi that consists of (1) 20% to 75% by weight of a pigment component, (2) 0.2% to 15% by weight of a surfactant component, (3) 20% to 75% by weight of water, and (4) 0.02% to 2% by weight of a biocidal component that comprises a polyoxymethyleneoxazolidine selected from the group consisting of (a) compounds having the structural formula

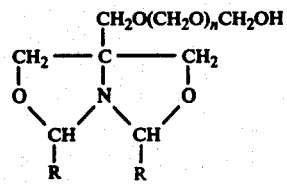

wherein each R represents hydrogen, alkyl of 1 to 6 carbon atoms, phenyl, halophenyl, or —(CH$_2$O)$_m$CH$_2$OH; m represents a number in the range of 0 to 2; and n represents a number in the range of 1 to 4;

(b) compounds having the structural formula

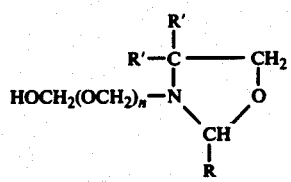

wherein each R' represents alkyl of 1 to 6 carbon atoms or —CH$_2$OH and R and n have the aforementioned significance; and (c) mixtures thereof.

2. An aqueous pigment dispersion as defined in claim 1 that contains from 0.1% to 1% by weight of said biocidal component.

3. An aqueous pigment dispersion as defined in claim 1 wherein the polyoxymethyleneoxazolidine has the structural formula

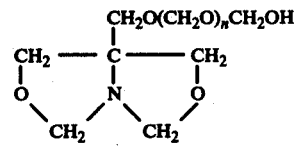

wherein n represents a number in the range of 1 to 4.

4. An aqueous pigment dispersion as defined in claim 1 wherein the pigment component comprises titanium dioxide.

5. An aqueous pigment dispersion as defined in claim 1 wherein the pigment component comprises an organic pigment.

6. An aqueous pigment dispersion as defined in claim 1 wherein the pigment component comprises a clay.

* * * * *